US007250295B2

(12) United States Patent
Hart et al.

(10) Patent No.: US 7,250,295 B2
(45) Date of Patent: Jul. 31, 2007

(54) PLANT CELLS ENCODING A PEPTIDE MIMOTOPE TO MYCOTOXIN DEOXYNIVALENOL AND USES THEREOF

(75) Inventors: Lynn Patrick Hart, Lansing, MI (US); James J. Pestka, East Lansing, MI (US); Qiaoping Yuan, Frederick, MD (US)

(73) Assignee: Board of Trustees of Michigan State University, East Lansing, MI (US)

( * ) Notice: Subject to any disclaimer, the term of this patent is extended or adjusted under 35 U.S.C. 154(b) by 477 days.

(21) Appl. No.: 10/118,708

(22) Filed: Apr. 9, 2002

(65) Prior Publication Data

US 2003/0165991 A1   Sep. 4, 2003

Related U.S. Application Data

(62) Division of application No. 09/626,821, filed on Jul. 27, 2000, now Pat. No. 6,537,762.

(60) Provisional application No. 60/146,643, filed on Jul. 30, 1999.

(51) Int. Cl.
*C12N 15/82*   (2006.01)
(52) U.S. Cl. ...................... 435/418; 800/279
(58) Field of Classification Search ............... 435/7.1; 530/329; 800/278, 298
See application file for complete search history.

(56) References Cited

U.S. PATENT DOCUMENTS

| | | | |
|---|---|---|---|
| 4,486,530 A | | 12/1984 | David et al. |
| 4,879,248 A | | 11/1989 | Chu et al. |
| 5,118,612 A | | 6/1992 | Chu et al. |
| 5,169,789 A | | 12/1992 | Bernstein et al. |
| 5,559,041 A | | 9/1996 | Kang et al. |
| 5,618,988 A | * | 4/1997 | Hauptmann et al. ........ 800/282 |
| 5,620,845 A | | 4/1997 | Gould et al. |
| 5,656,448 A | | 8/1997 | Kang et al. |
| 5,684,238 A | * | 11/1997 | Ausich et al. .............. 800/298 |
| 5,695,928 A | | 12/1997 | Stewart et al. |
| 5,728,587 A | | 3/1998 | Kang et al. |
| 5,736,369 A | * | 4/1998 | Bowen et al. .............. 800/293 |
| 5,767,368 A | * | 6/1998 | Zhong et al. ............... 800/279 |
| 5,846,745 A | | 12/1998 | Christensen et al. |

OTHER PUBLICATIONS

Yuan et al., Identification of Mimotope Peptides Which Bind To The Mycotoxin Deoxynivalenol-Specific Monoclonal Antibody, Applied and Environmental Microbiology, 65:3279-3286, 1999.*
Harris et al., Possible Role of Trichothecene Mycotoxins in Virulence of Fusarium graminearum on Maize, Plant Disease 83: 954-960, 1999.*
Proctor RH., Reduced Virulence of Gibberella zeae Caused By Disruption Of A Trichothecene Toxin Biosynthetic Gene, MPMI, 8: 593-601, 1995.*
Hightower et al, 1994, Plant Cell Rep. 13:295-299.*
De Bolle et al, 1996, Plant Mol. Biol. 31:993-1008.*
Pang et al, 1992, Gene 116:165-172.*
Okamoto et al, 1998, Plant Cell Physiol. 39:57-63.*
Allefs et al, 1995, Am. Potato J. 72:437-445.*
Bosch et al, 1994, Transgen. Res. 3:304-310.*
Hart et al., J. Agric. Food Chem. 31: 657-659 (1983).
Hart et al., Plant Dis. 66: 1133-1135 (1982).
Neish et al., Can. J. Plant Sci. 61: 811-815 (1981).
Betina, Chem. Biol. Interact. 71: 105-146 (1989).
Weber et al., Biochem. 31: 9350-9354 (1992).
Scott et al., Proc. Natl. Acad. Sci. USA 89: 5398-5402 (1992).
Casale et al., J. Agric. Food Chem. 36: 663-668 (1988).
Pestka et al., FoodTechnol. 49: 120-128 (1995).
Yuan et al., Appl. Environ. Microbiol. 63: 263-269 (1997).
Yamaguchi-Schinozaki et al., Plant Cell 6: 251-264 (1994).
Carrier et al., J. Immunol. Methods 181: 177-186 (1995).
Marin et al., In Toxicology 114: 67-79 (1996).
F. Chu et al., Appl. Environ. Microbiol. 37: 104-108 (1979).
Collawn et al., EMBO J. 10: 3247-3252 (1991).
Craig et al., J. Molec. Biol. 281: 183-201 (1998).
Laskowski et al., J. Appl. Cryst. 26: 283-291 (1993).

* cited by examiner

*Primary Examiner*—Anne Kubelik
(74) *Attorney, Agent, or Firm*—Ian C. McLeod

(57) ABSTRACT

The present invention provides transgenic plants cells that express a peptide mimotope of the non-peptide mycotoxin deoxynivalenol. In particular, the peptide mimotope competes with deoxynivalenol for binding to a monoclonal antibody and is antagonistic to the inhibitory effects of deoxynivalenol on in vitro protein synthesis. ransgenic plants expressing the peptide mimotype are resistant to deoxynivalenol.

2 Claims, 7 Drawing Sheets

Deoxynivalenol

Nivalenol

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Sequence
      encoding the DONPEP.2 peptide mimotope of
      deoxynivalenol

<400> SEQUENCE: 1
agttggggtc cttttccgtt t                                            21

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: DONPEP.2
      peptide mimotope of deoxynivalenol

<400> SEQUENCE: 2

Ser Trp Gly Pro Phe Pro Phe
 1               5

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Sequence
      encoding the DONPEP.12 peptide mimotope of
      deoxynivalenol

<400> SEQUENCE: 3
tcttggggtc cgcttccttt t                                            21

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: DONPEP.12
      peptide mimotope of deoxynivalenol

<400> SEQUENCE: 4

Ser Trp Gly Pro Leu Pro Phe
 1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: C430, the
      DONPEP.2 with a structurally flexible linker and a
      cysteine residue

<400> SEQUENCE: 5

Ser Trp Gly Pro Phe Pro Phe Gly Gly Gly Ser Cys
 1               5                  10

<210> SEQ ID NO 6
<211> LENGTH: 7
<212> TYPE: PRT

```
<213> ORGANISM: Artificial Sequence
<220> FEATURE:
<223> OTHER INFORMATION: Description of Artificial Sequence: A consensus
      sequence for peptide mimotopes of deoxynivalenol
<220> FEATURE:
<221> NAME/KEY: VARIANT
<222> LOCATION: (5)
<223> OTHER INFORMATION: can be any amino acid
<220> FEATURE:
<221> NAME/KEY: VARIANT
<222> LOCATION: (7)
<223> OTHER INFORMATION: can be any amino acid

<400> SEQUENCE: 6

Ser Trp Gly Pro Xaa Pro Xaa
  1               5

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Sense
      primer

<400> SEQUENCE: 7
gccaagctta gatcttggag ccttttttt ggag                             34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Antisense
      primer

<400> SEQUENCE: 8
ccggtcgacc tgtatgggat tttgctaaac aact                            34
```

PLANT CELLS ENCODING A PEPTIDE MIMOTOPE TO MYCOTOXIN DEOXYNIVALENOL AND USES THEREOF

CROSS-REFERENCE TO RELATED APPLICATION

This is a divisional application and the assignment document for the parent application Ser. No. 09/626,821 was filed on Jul. 27, 2000, now U.S. Pat. No. 6,537,762.

This application claims the benefit of U.S. Provisional Serial No. 60/146,643 filed Jul. 30, 1999.

STATEMENT REGARDING FEDERALLY SPONSORED RESEARCH OR DEVELOPMENT

This invention was supported by U.S. Department of Agriculture Research National Research Initiative grant 9702545 and Public Health Service grant E5-03358. The United States has certain rights in this invention.

BACKGROUND OF THE INVENTION (1) Field of the Invention

The present invention relates to a peptide mimotope of the non-peptide mycotoxin deoxynivalenol. In particular, the peptide mimotope competes with deoxynivalenol for binding to a monoclonal antibody, is antagonistic to the inhibitory effects of deoxynivalenol on in vitro protein synthesis, and does not elicit antibodies in mice that recognize the deoxynivalenol. The present invention also relates to a method that uses the peptide mimotope to determine whether corn, grains or mixed feed is contaminated with fungi that produces deoxynivalenol. The present invention further relates to transgenic plants resistant to deoxynivalenol.

(2) Description of Related Art

Deoxynivalenol (DON) or vomitoxin or dehydronivalenol is 12,13-epoxy-3,7,15-trichothec-9-en-8-one, which is a mycotoxin of the 12,13-epoxy-trichothecenes class of sesquiterpene mycotoxins. It is produced primarily by the fungus *Gibberella zeae* (Schwein.) Petch (anamorph=*Fusarium graminearum* Schwabe), which infects corn, small grains and mixed feeds (Hart et al., J. Agric. Food Chem. 31: 657-659 (183); Hart et al., Plant Dis. 66: 1133-1135 (1982); Neish et al., Can. J. Plant Sci. 61: 811-815 (1981)). At the cellular level, the primary toxic effect of DON is inhibition of protein synthesis by binding to the 60S ribosomal subunit, which interferes with peptidyltransferase (Betina, Chem. Biol. Interact. 71: 105-146 (1989); Weber et al., Biochem. 31: 9350-9354 (1992)). DON can cause anorexia and emesis in animals (Scott et al. Proc. natl. Acad. Sci. USA 89: 5398-5402 (1992)). Other toxic effects of DON include skin irritation, hemorrhaging, hematological changes, human lymphocyte blastogenesis impairment, radiomimetic effects, apoptosis and immunotoxicity (Scott et al. ibid.).

DON is primarily found as a contaminant in grains that are infected with the above fungi. It has also been implicated as a chemical warfare agent. Currently, the only means for eliminating DON from human and animal foodstuffs is to detect DON in food and to remove any contaminated foodstuffs from the food supply. Immunoassays offer several advantages compared to other analytical methods for detecting DON in foodstuffs. Following the development of the first monoclonal antibody to DON (Casale et al., J. Agric. Food Chem. 36: 663-668 (1988)), immunological methods, primarily enzyme-linked immunosorbant assay (ELISA), have been widely used for detection of DON (Pestka et al., Food Technol. 49: 120-128 (1995)). An immunoassay for trichothecenes such as DON is disclosed in U.S. Pat. No. 4,879,248 to Chu et al. and kit comprising the immunoassay is disclosed in U.S. Pat. No. 5,118,612 to Chu et al. The immunoassay and kit are either radio immunoassays (RIA) or enzyme-linked immunosorbant assay ELISA based on a competitive control that is DON. These immunological assays have advantages which include high specificity, ease of use, facile sample preparation, and good sensitivity.

The disadvantages of these immunoassays is that they require the user to handle purified DON which poses a toxicity risk to the user. In addition, chemical conjugation of DON to a carrier protein or an enzyme has low efficiency because it involves extensive modification and blocking stages and causes substantial bridge-group interferences and un-wanted cross-reactions (Casale et al., ibid.: Pestka et al., ibid.; Yuan et al., Appl. Environ. Microbiol. 63: 263-269 (1997)). Furthermore, DON is poorly immunogenic and when DON is conjugated to a carrier protein, it's immunogenicity is only marginally enhanced.

Therefore, it is desirable that an alternative to DON be developed. Preferably, the DON alternative would be non-toxic to the user, not require conjugation to a protein, and be highly immunogenic.

SUMMARY OF THE INVENTION

The present invention provides a peptide mimotope of the non-proteinaceous mycotoxin deoxynivalenol (DON). In particular, the peptide mimotope competes with DON for binding to a monoclonal antibody against the DON, is antagonistic to the inhibitory effects of DON on in vitro protein synthesis, and does not elicit antibodies in mice that recognize DON.

The peptide mimotope comprises amino acid sequence $SWGPX_1PX_2$ (SEQ ID NO:6) wherein $X_1$ is L, F, or analog thereof and $X_2$ is any amino acid or analog thereof. In particular species of the present invention, a peptide mimotope of DON is provided comprising the amino acid sequence SWGPFPF (SEQ ID NO:2), a peptide mimotope of DON comprising the amino acid sequence SWGPLPF (SEQ ID NO:4), or a peptide mimotope of DON comprising the amino acid sequence SWGPFPFGGGSC (SEQ ID NO:5). The peptide mimotope species are antagonistic to the inhibitory effects of DON on in vitro protein synthesis. In a preferred embodiment, the peptide mimotope is conjugated to a reporter for an immunological assay wherein the reporter is selected from the group consisting of alkaline phosphatase, horseradish peroxidase, or fluorescence molecule. In another preferred embodiment, the peptide mimotope is a part of a peptide or polypeptide. In particular, as a fusion polypeptide wherein the polypeptide is selected from the group consisting of alkaline phosphatase and horseradish peroxidase.

The present invention further provides a nucleic acid that encodes the peptide mimotope of DON comprising an amino acid sequence selected from the group consisting of SWGPLPF (SEQ ID NO: 2), SWGPFPF (SEQ ID NO: 4), and SWGPFPFGGGSC (SEQ ID NO: 5). In particular embodiments, the nucleic acid sequence is selected from the group consisting of SEQ ID NO: 1 and SEQ ID NO: 3.

The present invention also provides a clone in a microorganism expressing a peptide mimotope of DON comprising amino acid sequence $SWGPX_1PX_2$ (SEQ ID NO: 6) wherein $X_1$ is L, F, or analog thereof and $X_2$ is any amino acid or analog thereof. In particular species, the peptide mimotope comprises an amino acid sequence selected from the group consisting of SWGPFPF (SEQ ID NO: 2), SWGPLPF (SEQ ID NO: 4), and SWGPFPFGGGSC (SEQ ID NO: 5). In particular, the peptide mimotope expressed by the clone is antagonistic to the inhibitory effects of DON on in vitro protein synthesis. For the clone expressing the peptide mimotope, the peptide mimotope is encoded by a nucleic acid in a plasmid or by a nucleic acid in a recombinant virus vector such as a bacteriophage and the peptide mimotope can be expressed as an isolated peptide or as a part of a fusion polypeptide. Furthermore, the microorganism containing the clone expressing the peptide mimotope can be selected from the group consisting of bacteria and yeasts.

The present invention further provides a transgenic plant containing a nucleic acid that expresses a peptide mimotope of DON that binds to a monoclonal antibody against DON and is antagonistic to the inhibitory effects of DON on in vitro protein synthesis. In particular, the present invention provides a transgenic plant that expresses a peptide mimotope of DON comprising amino acid sequence SWGPX$_1$PX$_2$ wherein X$_1$ is L, F, or analog thereof and X$_2$ is any amino acid or analog thereof. In particular species, the amino acid sequence is selected from the group comprising SWGPFPF (SEQ ID NO: 2), SWGPLPF (SEQ ID NO: 4), and SWGPFPFGGGSC (SEQ ID NO: 5). Further, the peptide mimotope that is expressed can be as an isolated peptide or as a part of a fusion polypeptide.

The present invention also provides an improvement in a method for determining whether a sample contains DON which comprises providing a monoclonal antibody against the DON, reacting the monoclonal antibody with the sample in a reaction mixture containing a labeled DON as a competitor, and determining whether the sample contains DON, wherein the improvement is providing as the competitor a peptide mimotope of DON. In particular, the peptide mimotope has amino acid sequence SWGPX$_1$PX$_2$ (SEQ ID NO: 6) wherein X$_1$ is L, F, or analog thereof and X$_2$ is any amino acid or analog thereof. In particular species, the amino acid sequence is selected from the group consisting of SWGPFPF (SEQ ID NO: 2), SWGPLPF (SEQ ID NO: 4), and SWGPFPFGGGSC (SEQ ID NO: 5). Further, the peptide mimotope can be as an isolated peptide or as a part of a fusion polypeptide.

The present invention also provides a method for determining whether a sample contains deoxynivalenol (DON) which comprises: (a) incubating in a reaction the sample, a monoclonal antibody against the DON, and a peptide mimotope which is a competitor of the DON for the monoclonal antibody; (b) detecting in the reaction a complex consisting of the DON bound by the monoclonal antibody and a complex formed by the mimotope and monoclonal antibody; and (c) comparing an amount of each of the complexes wherein a decrease in the amount of the complex comprising the peptide mimotope indicates that the sample contains DON. In particular, the peptide mimotope comprises amino acid sequence SWGPX$_1$PX$_2$ (SEQ ID NO: 6) wherein X$_1$ is L, F, or analog thereof and X$_2$ is any amino acid or analog thereof. In particular species, the amino acid sequence is selected from the group consisting of SWGPFPF (SEQ ID NO: 2), SWGPLPF (SEQ ID NO: 4), and SWGPFPFGGGSC (SEQ ID NO: 5). In a preferred embodiment of the method, the monoclonal antibody is produced by hybridoma cell line 6F5. The method further comprises the peptide mimotope which is conjugated to an enzyme selected from the group consisting of horseradish peroxidase and alkaline phosphatase; the peptide mimotope conjugated to a fluorescent reporter; and the peptide mimotope wherein the amino acid of the peptide mimotope is conjugated to an enzyme selected from the group consisting of horseradish peroxidase and alkaline phosphatase to make a fusion protein. Alternatively, the peptide mimotope can be part of a fusion polypeptide wherein the polypeptide is an enzyme that is used as a reporter enzyme in immunoassays, in particular alkaline phosphatase or horseradish peroxidase.

The present invention also provides a kit for determining whether a sample contains deoxynivalenol (DON) comprising: (a) a monoclonal antibody against the DON; (b) a peptide mimotope of the DON that competes with DON for binding to the monoclonal antibody; and (c) instructions for using the kit. In particular, the mimotope comprises amino acid sequence SWGPX$_1$PX$_2$ (SEQ ID NO: 6) wherein X$_1$ is L, F, or analog thereof and X$_2$ is any amino acid or analog thereof. In particular species, the peptide mimotope of the kit comprises an amino acid sequence selected from the group consisting of SWGPFPF (SEQ ID NO: 2), SWGPLPF (SEQ ID NO: 4), and SWGPFPFGGGSC (SEQ ID NO: 5). In the preferred embodiment, the monoclonal antibody is produced by hybridoma cell line 6F5. The kit further comprises the peptide mimotope which is conjugated to an enzyme selected from the group consisting of horseradish peroxidase and alkaline phosphatase; the peptide mimotope conjugated to a fluorescent reporter; and a fusion protein wherein the amino acid sequence comprising the peptide mimotope is conjugated to an enzyme selected from the group consisting of horseradish peroxidase and alkaline phosphatase. Alternatively, the peptide mimotope can be part of a fusion polypeptide wherein the polypeptide is an enzyme that is used as a reporter enzyme in immunoassays, in particular alkaline phosphatase or horseradish peroxidase.

The present invention further provides a method for making a plant resistant to deoxynivalenol (DON) comprising introducing into the plant plant's genome a nucleic acid that encodes a peptide mimotope, which binds to a monoclonal antibody against DON and is antagonistic to the inhibitory effects of DON on in vitro protein synthesis, which is operably linked to a transcription promoter. In particular, the peptide mimotope comprises amino acid sequence SWGPX$_1$PX$_2$ (SEQ ID NO: 6) wherein X$_1$ is L, F, or analog thereof and X$_2$ is any amino acid or analog thereof. In a particular species, the peptide mimotope comprises an amino acid sequence selected from the group consisting of SWGPFPF (SEQ ID NO: 2), SWGPLPF (SEQ ID NO: 4), and SWGPFPFGGGSC (SEQ ID NO: 5). The peptide mimotope can be expressed as an isolated peptide or as a part of a fusion polypeptide.

The present invention also provides a method for treating an organism exposed to deoxynivalenol (DON) comprising treating the organism with a peptide mimotope of DON which is antagonistic to the inhibitory effects of DON on in vitro protein synthesis. In particular, the peptide mimotope comprises amino acid sequence SWGPX$_1$PX$_2$ (SEQ ID NO: 6) wherein X$_1$ is L, F, or analog thereof and X$_2$ is any amino acid or analog thereof. In a particular species, the peptide mimotope comprises an amino acid sequence selected from the group consisting of SWGPFPF (SEQ ID NO: 2), SWGPLPF (SEQ ID NO: 4), and SWGPFPFGGGSC (SEQ ID NO: 5). The treatment may be given orally, topically, or intravenously. Furthermore, the treatment can comprise a peptide mimotope of DON, which is a vaccine that elicits antibodies against DON. The vaccine can be administered either as a therapeutic treatment to an animal or person displaying symptoms of exposure to DON or as a prophylactic treatment to prevent symptoms caused by a subsequent exposure to DON. The peptide mimotope can be the isolated peptide or as a part of a fusion polypeptide.

OBJECTS

It is therefore an object of the present invention to provide a peptide mimotope of deoxynivalenol (DON) for use in immunological assays for detecting DON in a sample.

It is also an object of the present to provide a transgenic plant which is resistant to the affects of DON.

It is a further object of the present invention to provide a method for treating an animal or person exposed to DON.

DESCRIPTION OF PREFERRED EMBODIMENTS

All patents, patent applications, and literature references cited in this specification are hereby incorporated herein by reference in their entirety. In case of conflict, the present description, including definitions, will control.

To promote a better understanding of the present invention, the following terms are defined.

The term "mimotope" means a molecule which has a conformation that has a topology equivalent to the epitope of which it is a mimic. The mimotope binds to the same antigen-binding region of an antibody which binds immunospecifically to a desired antigen. Generally, a mimotope will elicit an immunological response in a host that is reactive to the antigen to which it is a mimic.

The term "mimetic" is a related mimotope which means a molecule which competes with the antigen for binding to the antibody but which does not elicit an antibody in a host that is reactive against the antigen. The present invention is a mimetic.

The term "monoclonal antibody" as used herein refers to antibodies produced by a single line of hybridoma cells all directed towards one epitope on a particular antigen. A hybridoma is a clonal cell line that consists of hybrid cells formed by the fusion of a myeloma cell and a specific antibody-forming cell. In general, monoclonal antibodies are of mouse origin; however, monoclonal antibody also refers to a clonal population of an antibody made against a particular antigen or epitope of an antigen produced by phage display technology or method that is equivalent to phage display or hybrid cells of non-mouse origin.

The term "antigen" as used herein refers to a substance which stimulates production of antibody or sensitized cells during an immune response. An antigen consists of one or more epitopes, each epitope of which is capable of causing the production of an antibody against the particular epitope.

The term "epitope" as used herein refers to an immunogenic region of an antigen which is recognized by a particular antibody molecule. In general, an antigen will possess one or more epitopes, each capable of binding an antibody that recognizes the particular epitope.

Amino acids are represented herein by the single letter or triplet code wherein alanine is A or Ala, arginine is R or Arg, asparagine is N or Asn, aspartic acid is D or Asp, cysteine is C or Cys, glutamine is Q or Gln, glutamic acid is E or Glu, glycine is G or Gly, histidine is H or His, isoleucine is I or Ile, leucine is L or Leu, lysine is K or Lys, methionine is M or Met, phenylalanine is F or Phe, proline is P or Pro, serine is S or Ser, threonine is T or Thr, tryptophan is W or Trp, tyrosine is Y or Tyr, and valine is V or Val.

The nucleotides are represented herein by A for adenosine, G for guanosine, C for cytosine, and T for thymidine.

Figure 1A:
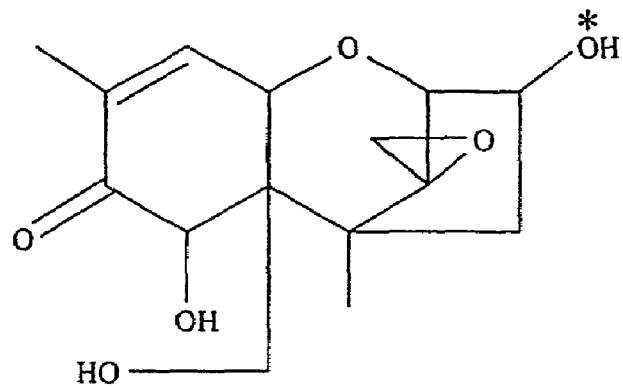
FIG. 1A shows a two-dimensional representation of DON. The asterisk indicates the site of conjugation of the carrier protein, e.g., BSA, to DON.
Figure 1B:
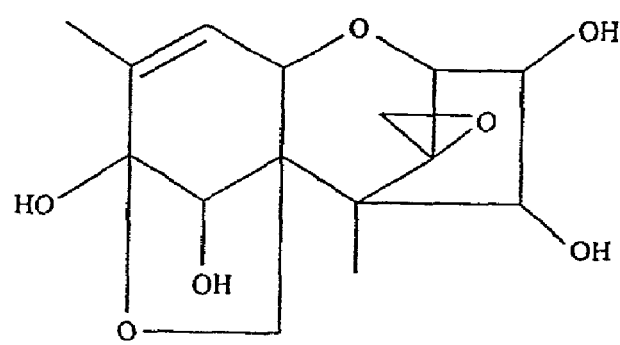
FIG. 1B shows a two-dimensional representation of nivalenol, an analog of DON whose three-dimensional structure is known.

The present invention provides peptide mimotopes of the non-peptide toxin, deoxynivalenol (DON). DON has the two-dimensional structure shown in FIG. 1A. The peptide mimotopes have a topological structure that mimics the three-dimensional structure of DON. As shown in FIG. 1E, the three-dimensional structure of nivalenol, an analog of DON which has the two-dimensional structure shown in FIG. 1B, which can be aligned along the peptide mimotope main chain atoms from amino acid residue 2 to 5, i.e., TrpGlyPro (WGP). The close structural alignment is sufficient to enable the peptide mimotopes to be recognized by an anti-DON monoclonal antibody, mAB 6F5, and effectively compete with DON for binding to the anti-DON monoclonal antibody (FIGS. 2-5).

Monoclonal antibody mAB 6F5 from hybridoma cell line mAB 6F5 was prepared as described in Casale et al., J. Agric. Food Chem. 36: 663-668 (1988). Monoclonal antibody mAB 6F5 is available from Michigan State University and is commercially available from Neogen Corporation, 620 Lesher Place, Lansing, Mich. 48912. Alternatively, hybridomas that produce mAB against DON can be prepared as taught in Casale et al., J. Agric. Food Chem. 36: 663-668 (1988). Hybridoma clones that produce monoclonal antibodies against DON are then screened with a labeled peptide mimitope which enables those hybridoma clones that react against the peptide mimotope to be identified.

The toxic effect of DON is caused by its binding to a particular site on the 60S ribosome, which inhibits 60S ribosome function, thereby preventing protein synthesis. Competition experiments between DON and the peptide mimotopes indicate that the peptide mimotopes bind to the same site on the 60S ribosome as DON (FIG. 7); however, in contrast to when DON is bound, the peptide mimotopes do not inhibit the function of the 60S ribosome. Thus, the present invention is both a mimic of the DON epitope that is recognized by the anti-DON monoclonal antibody and a competitor that binds to the same site on the 60S ribosome as DON, but without DON's inhibitory effect. Since there are few examples of mimotopes of non-proteinaceous chemicals other than biotin or carbohydrates, it was uncertain whether a peptide sequence could be found that would mimic DON. Therefore, it was unexpected that the peptide mimotopes which bind to the monoclonal antibody against DON would be antagonistic to the toxic effects of DON on protein synthesis indicating it was a mimetic.

In general, the present invention provides peptide mimotopes that have an amino acid sequence of $SWGPX_1PX_2$ (SEQ ID NO: 6) wherein the amino acid sequence mimics the DON epitope that is bound by anti-DON monoclonal antibody mAB 6F5 and wherein $X_1$ and $X_2$ is each any amino acid or analog thereof, preferably wherein $X_1$ is an amino acid or analog thereof which has a side chain that is a hydrogen or alkyl, most preferably, wherein $X_1$ is L, F, or analog thereof. The SWGP is the portion of the peptide that can be aligned with the structure of nivalenol and mimics the nivalenol structure. In particular, the present invention provides a peptide mimotope that has the amino acid sequence selected from the group consisting of SWGPFPF (SEQ ID NO: 2), which is peptide DONPEP.2; SWGPLPF (SEQ ID NO: 4), which is peptide DONPEP.12; and, SWGPF-PFGGGSC (SEQ ID NO: 5), which is peptide C430 comprising the DONPEP.2 amino acid sequence coupled to amino acid sequence GGGSC. Each of the aforementioned peptide mimotopes are artificial peptide sequences that are not naturally produced in nature. The peptide mimotopes can be made in vitro using any one of the peptide synthesis methods which are well known in the art, e.g., Fmoc peptide synthesis chemistry. For particular applications it is desirable to produce the peptide mimotope in vivo; therefore, the peptide DONPEP.2 is encoded by the nucleic acid sequence 5-AGTTGGGGTCCTTTTCCGTTT-3 (SEQ ID NO: 1) and peptide DONPEP.12 is encoded by nucleic acid sequence 5'-TCTTGGGGTCCGCTTCCTTTT-3' (SEQ ID NO: 3). Producing the peptide mimotope in vivo is particularly desirable when the peptide mimotope is to be expressed as a part of a fusion peptide or polypeptide. For example, the phage clones disclosed herein express a chimeric polypeptide that contains the peptide mimotope amino acid sequence within and covalently linked to the amino acid sequence for the minor coat protein of phage M13, and DONPEP-AP disclosed herein is a chimeric polypeptide wherein the peptide mimotope amino acid sequence is between and covalently linked to the amino acid sequence for the minor coat protein signal sequence and the amino acid sequence for alkaline phosphatase. In general, chimeric fusion polypeptides, particularly large fusion polypeptides, are more economically produced in vivo than in vitro.

The peptide mimotope can be synthetically produced by chemical synthesis methods which are well known in the art, either as an isolated peptide or as a part of another peptide or polypeptide. Alternatively, the peptide mimotope can be produced in a microorganism which produces the peptide mimotope which is then isolated and if desired, further purified. The isolated or purified peptide mimotope can be used as a control or competitor in immunoassays for detecting DON in food samples, or because it competes with DON for binding to the 60S ribosome, the isolated or purified peptide mimotope can be used in therapies for treating animals or humans exposed to DON. Thus, the peptide mimotope can be produced in microorganisms such as bacteria, yeast, or fungi; in a eukaryote cells such as a mammalian or an insect cells; or, in a recombinant virus vector such as adenovirus, poxvirus, herpesvirus, Simliki forest virus, baculovirus, bacteriophage, sindbis virus, or sendai virus. Suitable bacteria for producing the peptide mimotope include *Escherichia coli, Bacillus subtilis*, or any other bacterium that is capable of expressing peptides such as the peptide mimotope. Suitable yeast types for expressing the peptide mimotope include, but is not limited to *Saccharomyces cerevisiae, Schizosaccharomyces pombe, Candida*, or any other yeast capable of expressing peptides. Methods for using the aforementioned bacteria, recombinant virus vectors, eukaryote cells to produce peptides are well known in the art.

To produce the peptide mimotope, the nucleic acid encoding the peptide mimotope is in a plasmid and the nucleic acid is operably linked to a promoter which effects the expression of the peptide mimotope in a microorganism. Suitable promoters include, but are not limited to, T7 phage promoter, T3 phage promoter, β-galactosidase promoter, and the Sp6 phage promoter. Expression of the peptide mimotope in a microorganism enables the peptide mimotope to be produced using fermentation technologies which are used commercially for producing large quantities of peptides. Methods for isolating and purifying peptides are well known in the art and include methods such as gel filtration, affinity chromatography, ion exchange chromatography, or centrifugation.

To facilitate isolation of the peptide mimotope, a fusion polypeptide is made wherein the peptide mimotope is translationally fused (covalently linked) to a heterologous polypeptide which enables isolation by affinity chromatography. Preferably, a fusion polypeptide is made using one of the expression systems infra. For example, the nucleic acid sequence encoding the peptide mimotope is linked at either the 5' end or 3' end to a nucleic acid encoding a heterologous polypeptide. The nucleic acids are covalently linked in the proper codon reading frame to enable production of a fusion polypeptide wherein the amino and/or carboxyl terminus of the peptide mimotope is translationally fused to the heterologous polypeptide which allows for the simplified recovery of the fusion polypeptide. The fusion polypeptide can also prevent the mimotope polypeptide from being degraded during purification. While the fusion polypeptide is efficacious, as shown by the results herein for the phage clones or DONPEP-AP, in some instances it can be desirable to remove the heterologous polypeptide after purification. Therefore, it is also contemplated that the fusion polypeptide comprise a cleavage site at the junction between the peptide mimotope and the heterologous polypeptide. The cleavage site consists of an amino acid sequence that is cleaved with an enzyme specific for the amino acid sequence at the site. Cleavage sites that are contemplated include, but are not limited to, the enterokinase cleavage site which is cleaved by enterokinase, the factor Xa cleavage site which is cleaved by factor Xa, and the GENENASE cleavage site which is cleaved by GENENASE (GENENASE is a trademark of New England Biolabs, Beverly, Mass.). The following are methods for producing the peptide mimotope as a fusion polypeptide or as an isolated peptide mimotope free of the heterologous polypeptide.

An example of a procaryote expression system for producing the peptide mimotope is the Glutathione S-transferase (GST) Gene Fusion System available from Amersham Pharmacia Biotech, Piscataway, N.J., which uses the pGEX-4T-1 expression vector plasmid. The nucleic acid encoding the peptide mimotope is fused in the proper codon reading frame with the nucleic acid encoding the GST polypeptide. The GST polypeptide allows the rapid purification of the fusion polypeptide using glutathione Sepharose 4B affinity chromatography. After purification, the GST can be removed by cleavage with a site-specific protease such as thrombin or factor Xa to produce the mimotope free of the GST polypeptide. The peptide mimotope free of the GST polypeptide is produced by a second round of glutathione Sepharose 4B affinity chromatography.

Another method for producing the peptide mimotope is a method which links in-frame the nucleic acid encoding the peptide mimotope to a nucleic acid encoding polyhistidine, preferably encoding six histidine residues, to produce a peptide mimotope-polyhistidine fusion polypeptide. The polyhistidine allows purification of the fusion polypeptide by metal affinity chromatography, preferably nickel affinity chromatography. To produce the peptide mimotope free of the polyhistidine, a cleavage site such as an enterokinase cleavage site is fused in the proper reading frame between the codons encoding the polyhistidine and the codons encoding the peptide mimotope. Thus, the peptide mimotope free of the polyhistidine is made by removing the polyhistidine by cleavage with enterokinase. A second round of metal affinity chromatography which binds the free polyhistidine results in the peptide mimotope free of the polyhistidine. The Xpress System, available from Invitrogen, Carlsbad, Calif., is an example of a commercial kit which is available for making and then isolating polyhistidine fusion polypeptides.

In a method further still, the pMAL Fusion and Purification System available from New England Biolabs can be used to make a fusion polypeptide wherein a maltose binding protein is fused to the peptide mimotope. The maltose binding protein facilitates isolation of the fusion polypeptide by amylose affinity chromatography. The maltose binding protein can be linked to the peptide mimotope by one of the above mentioned cleavage sites which enables the peptide mimotope to be made free of the maltose binding protein.

Figure 5:
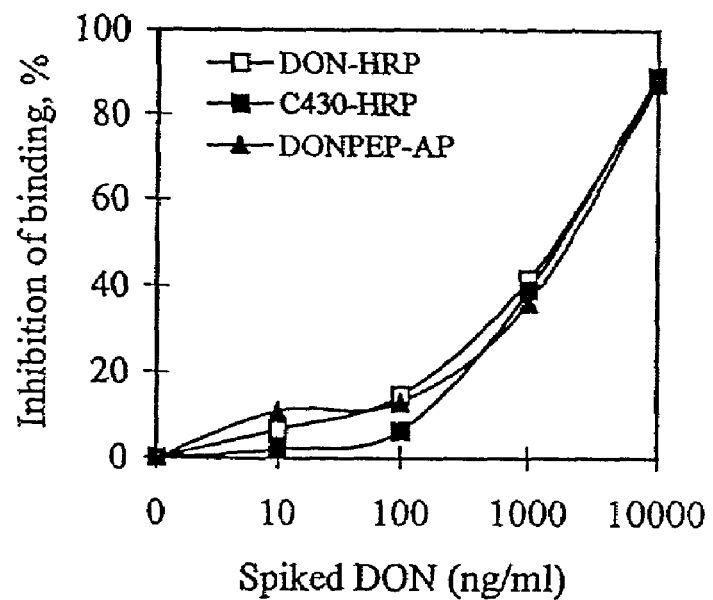
FIG. 5 shows the use of C430 HRP and DONPEP-AP in a DON immunoassay (CD-ELISA) performed with wheat extract spiked with DON. Immulon-4 microtiter wells were coated with mAB 6F5 and DON-HRP was used as a positive control.
Figure 6:
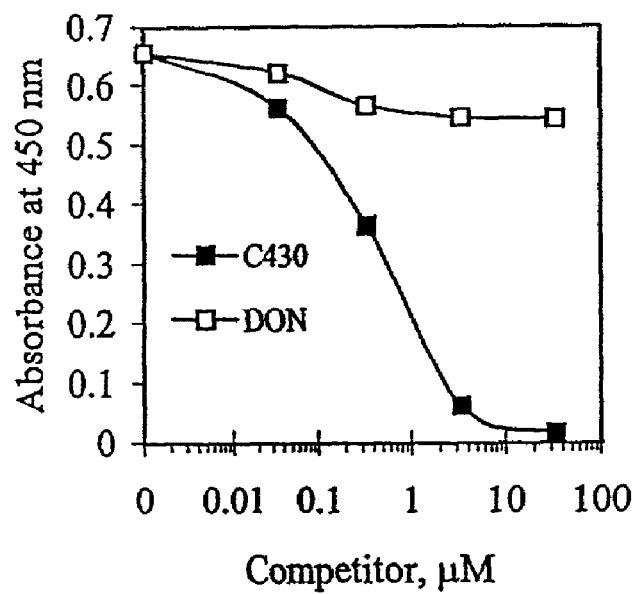
FIG. 6 shows the specificity of antibody obtained from C430-BSA-immunized mice. DON and C430 at various concentrations were used to inhibit the binding of antisera to immobilized DONPEP.2 phage. Bound mouse antibodies were detected with HRP-conjugated goat anti-mouse IgG, and the amounts of these antibodies were measured by absorbance.
Figure 7:
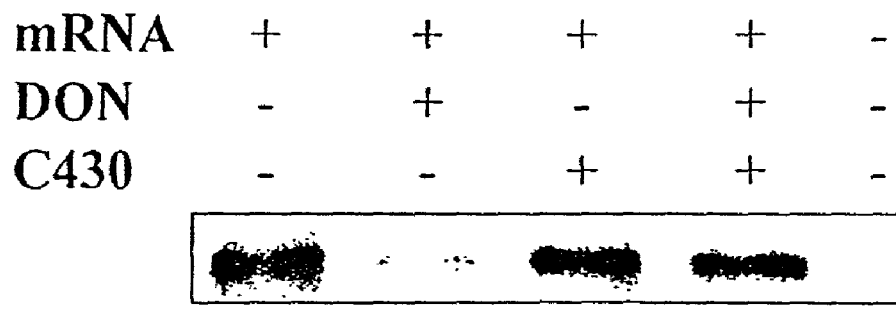
FIG. 7 shows the effects of DON (3.4 µM) and synthetic peptide C430 (3.4 µM) on protein synthesis in vitro with rabbit reticulocyte lysate. The translation template was γ-globulin mRNA. The plus and minus signs indicate which reagents were added.

It is particularly desirable that the peptide mimotope be a part of another peptide or polypeptide, particularly an enzyme which is used as a reporter in immunological assays. Such reporter enzymes include, but are not limited to, alkaline phosphatase or horseradish peroxidase. As shown herein by DONPEP-AP, the peptide mimotope was fused with alkaline phosphatase, a reporter enzyme commonly used in immunological assays. As shown in FIG. 5, the DONPEP-AP was useful as a DON competitor in immunological assays for detecting DON in wheat extracts. DONPEP-AP can be used in other immunological assays for determining whether a corn, grain, or mixed feed sample is contaminated with DON. The peptide mimotope can also be fused to other heterologous polypeptides which facilitate isolation or handling of the peptide mimotope in immunological assays. An example of such a heterologous polypeptide includes, but is not limited to, the minor coat protein g3p of filamentous phage M13. Thus, the heterologous polypeptides that can be used to make fusion polypeptides include, but is not limited to, the minor coat protein g3p of filamentous phage M13, which was used to make phage clones DONPEP.1, DONPEP.2, DONPEP.3, DONPEP.4 and DONPEP.12 containing the mimotope peptide sequence therein, and alkaline phosphatase, which was used to make DONPEP-AP. Preferably, the fusion polypeptide is produced in a recombinant bacterium or eukaryote expression vector as disclosed supra. for producing the peptide mimotope.

Further, the mimotope peptide, either by itself or as part of a fusion polypeptide, can be chemically conjugated to a carrier protein. Carrier proteins include, but are not limited to, bovine serum albumen (BSA), and reporter enzymes which include, but are not limited to, horseradish peroxidase or alkaline phosphatase. Further, the peptide mimotope or fusion peptide comprising the peptide mimotope can be chemically conjugated to fluorescence reporter molecules which include, but are not limited to, fluorescein or R-phycoerythrin. Methods for conjugating carrier proteins, enzymes, and fluorescence reporter molecules to peptides and fusion polypeptides are well known in the art.

The peptide mimotopes, either alone, conjugated to a carrier protein or fluorescent reporter molecule, or as a component of a fusion polypeptide are useful as standard and conjugates in immunoassays such as ELISAs and RIAS, which are used to determine whether a food sample is contaminated with DON. Currently, in such immunoassays, DON, which is toxic to the user, is used as a control or as a competitor. The immunoassays rely upon detection techniques which require DON to be conjugated to a carrier protein or reporter enzyme. Conjugating DON to a carrier protein or reporter enzyme has been difficult and the conjugation methods which are used require chemicals that are toxic to the user. Therefore, because the peptide mimotopes are non-toxic, the peptide mimotopes provide a significant advantage over DON. In particular, they are non-toxic to the user when used as a control or competitor in immunoassays, they are easier to conjugate to reporter enzymes than DON and conjugation does not require toxic chemicals, and unlike DON, they can be genetically fused to various reporter enzymes and produced by fermentation or other methods in large quantities thereby significantly reducing the costs associated with providing immunoassays for detecting DON. Thus, the immunoassays of the present invention use either the peptide mimotopes alone or the peptide mimotopes conjugated to a carrier protein or enzyme, or genetically fused to a reporter enzyme such as alkaline phosphatase or horseradish peroxidase, or conjugated to a reporter fluorescence molecule.

In general, the immunoassays are performed using an enzyme-linked immunosorbent assay (ELISA) embodiment and can be either a competitive direct ELISA (CD-ELISA) or competitive indirect ELISA (CI-ELISA). To perform a CD-ELISA, a microtiter plate is provided containing a plurality of wells wherein a first well or series of wells contains a monoclonal antibody against DON immobilized to the surface therein, preferably the monoclonal antibody is mAB 6F5. To prevent non-specific binding in the subsequent steps, it is preferable that the wells be treated with a blocking agent such as a 10% solution of non-fat milk. Next, a limiting dilution series of an aliquot of the sample are mixed with an equal volume of an appropriate dilution of the peptide mimotope and the mixture added to the wells containing the bound monoclonal antibody. Preferably, the mimotope peptide is conjugated to a carrier protein or is part of a fusion polypeptide. The DON in the sample and the peptide mimotope compete for binding to the monoclonal antibody. The ELISA is incubated for a time sufficient for monoclonal antibody-DON complexes to form. In general, an incubation time of about an hour at a temperature between about room temperature and 37° C. Afterwards, the wells are washed to remove any unbound material. The wells are then incubated with a labeled antibody or labeled monoclonal antibody that binds to the carrier protein or fusion polypeptide to form a complex which can be detected when the labeled monoclonal or polyclonal antibody is conjugated to a reporter ligand such as horseradish-peroxidase or alkaline phosphatase. Preferably, the incubation is for about an hour at a temperature between about room temperature and 37° C. A detectable signal from the reporter indicates the sample does not contain DON whereas an absence of a signal indicates that the sample contains DON which had bound all of the monoclonal antibody, thereby preventing the peptide mimotope from binding the monoclonal antibody immobilized in the wells. Alternatively, the second monoclonal or polyclonal antibody can be conjugated to reporter ligands such as a fluorescing ligand, biotin, colored latex, colloidal gold magnetic beads, radioisotopes or the like. When the fusion polypeptide comprises a reporter enzyme such as alkaline phosphatase, the antibody-mimotope peptide complex can be detected directly without the need for a labeled antibody. In either case, detection is by methods well known in the art for detecting the particular reporter ligand.

To perform a CI-ELISA, a microtiter plate is provided containing a plurality of wells wherein a first well or series of wells contains the peptide mimotope, the peptide mimotope conjugated to a carrier protein, or fusion polypeptide comprising the peptide mimotope is immobilized to the surface therein. To prevent non-specific binding in the subsequent steps, it is preferable that the wells be treated with a blocking agent such as a 10% solution of non-fat milk. Next, a limiting dilution series of an aliquot of the sample are added to the wells containing the bound peptide mimotopes along with a constant amount of a monoclonal antibody, preferably the mAB 6F5 monoclonal antibody. The DON in the sample and the peptide mimotope bound to the well surfaces compete for binding to the monoclonal antibody. The ELISA is incubated for a time sufficient for antibody-DON complexes to form. In general, an incubation time of about an hour at a temperature between about room temperature and 37° C. Afterwards, the wells are washed to remove any unbound material. The amount of monoclonal antibody that is bound to the immobilized mimotope peptides in the well is determined by incubating the wells with a labeled antibody or labeled monoclonal antibody that binds to the monoclonal antibody to form a complex that can be detected when the labeled monoclonal or polyclonal antibody is conjugated to a reporter ligand such as horseradish-peroxidase or alkaline phosphatase. Preferably for about an hour at a temperature between about room temperature and 37° C. A detectable signal from the reporter indicates the sample does not contain DON whereas an absence of a signal indicates that the sample contains DON which had bound all of the monoclonal antibody, thereby preventing the monoclonal antibody from binding the peptide mimotope immobilized in the wells. The intensity of the signal provides an estimate of the relative concentration of DON in the sample. Alternatively, the second monoclonal or polyclonal antibody can be conjugated to reporter ligands such as a fluorescing ligand, biotin, colored latex, colloidal gold magnetic beads, radioisotopes or the like. In an alternative further, the monoclonal antibody can be labeled with a reporter in which case the bound monoclonal antibody can be detected directly without the need for a labeled antibody. In either case, detection is by methods well known in the art for detecting the particular reporter ligand.

Instead of an ELISA, the peptide mimotopes can be used in a radio immunoassay (RIA) for detecting DON in a sample. The RIA procedure involves incubation of a monoclonal antibody against the DON, preferably mAB 6F5, simultaneously with a solution of unknown sample or known standard, and a constant amount of radioactively labeled peptide mimotope or fusion polypeptide. After separation of the free peptide mimotope or fusion polypeptide from bound peptide mimotope or fusion polypeptide, the radioactivity in the respective fractions is determined. The concentration of DON in the unknown sample is determined by comparing results to a standard curve. Several known methods, including the ammonium sulfate precipitation method, double antibody technique, solid phase RIA method in which immunoglobulin G (IgG) is conjugated to CNBr-activated SEPHAROSE gel (Pharmacia Biotech, Piscataway, N.J.), a dextran-coated charcoal Column and albumen-coated charcoal, is used for the separation of free from bound peptide mimotope or fusion polypeptide in the RIA. Radioactivity is determined in a liquid scintillation counter in 5 ml of AQUASOL (a product of New England Nuclear Corp., Boston, Mass.) for aqueous solutions.

In a further embodiment of the present invention, the peptide mimotope or fusion polypeptide is coupled to an energy donor fluorophore and the monoclonal antibody is coupled to an energy acceptor or quencher fluorophore. The quencher fluorophore is attached to a monoclonal antibody against DON, preferably mAB 6F5, such that when the peptide mimotope or fusion polypeptide binds the antibody, the quencher and reporter dye are in close proximity and the reporter dye is prevented from fluorescing. Therefore, when a sample does not contain DON, all of the peptide mimotope or fusion polypeptide is bound by the monoclonal antibody. Since the quencher and reporter dyes are in close proximity, the quencher prevents the reporter dye from fluorescing. However, when a sample contains DON, the DON competes with the peptide mimotope of fusion polypeptide for the antibody, which results in some peptide mimotope or fusion polypeptide molecules remaining unbound. Because these unbound peptide mimotope or fusion polypeptide molecules are no longer in close proximity to the quencher on the antibody, the reporter dye on these molecules will fluoresce. The intensity of fluorescence is directly proportional to the amount of DON in the sample. Fluorescence can be detected with an ABA Prism Sequence Detector or TAQMAN LS-50B PCR Detection System (both available from Perkin- Elmer Applied Biosystems), or other detector that is used to detect fluorescence. Alternatively, the peptide mimotope or fusion polypeptide is coupled to an energy acceptor fluorophore and the monoclonal antibody is coupled to the energy transfer fluorophore. The result would be the same. Preferably, the fluorophore is selected from the group consisting of fluorescein, 5-carboxyfluorescein (FAM), 2'7'-dimethoxy-4', 5'-dichloro-6-carboxyfluorescein (JOE), rhodamine, 6-carboxyrhodamine (R6G), N,N,N',N'-tetramethyl-6-carboxyrhodamine (TAMRA), 6-carboxyl-X-rhodamine (ROX), 4-(4'-dimethylaminophenylazo) benzoic acid (DABCYL), tetrachloro-6-carboxyl-fluorescein (TET), VIC, and 5-(2'-aminoethyl)aminonaphthalene-1-sulfonic acid (EDANS). This embodiment can be performed in a small reaction volume, does not need to rely on microtiter plates, and enables the assay results to be known instantaneously.

Since the ability to test samples in the field for DON contamination is very important, the method of the present invention further includes rapid immunodiffusion based methods and apparatuses for detecting DON in a sample. For example, a device containing the peptide mimotope, either as the peptide or as a fusion polypeptide is irreversibly fixed to a solid support. A solution containing the test sample is admixed with a solution containing a monoclonal antibody against DON, preferably mAB 6F5, conjugated to a reporter and a solution containing the solid support containing the mimotope. The admixture is then applied to a porous sheet material incorporating a chromogen and a substrate for the reporter, while keeping the support containing the mimotope out of contact with the porous sheet material. If the sample contains DON, the DON complexes with the antibody conjugate, which causes a color reaction on the porous sheet material. If the sample does not contain DON, the antibody is completely bound by the peptide mimotope or fusion polypeptide on the solid support. Since there is no antibody in solution, there is no color reaction. This method is disclosed in U.S. Pat. No. 5,846,745 to Christensen et al. The present invention can be used solid phase immunodiffusion assays such as those disclosed in U.S. Pat. No. 5,169,789 to Berstein. The above methods are provided as examples thus, other rapid immunoassays which are well known in the art are also within the scope of the present invention.

Thus, the present invention can be provided as a kit that comprises any one of the methods described above or in U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486,530 to David et al., and U.S. Pat. No. 4,786,589 to Rounds et al. While the aforementioned disclose particular rapid immunodiffusion methods, the present invention is not to be construed to be limited to the aforementioned. It is within the scope of the present invention to embrace derivations and modifications of the aforementioned.

When the peptide mimotopes are conjugated to an appropriate compound or chemical that facilitates entry of the peptide mimotopes into the cell of the host, the peptide mimotopes can be used as a treatment for plants, animals or people exposed to DON. Alternatively, the peptide mimotope can be a part of a peptide or polypeptide, i.e., fusion polypeptide or polypeptide, that facilitates entry of the peptide mimotope into the cell. The peptide mimotope in any of the aforementioned forms can be administered either topically, orally, or by injection.

The present invention further includes transgenic plants that express the peptide mimotope, either as an isolated peptide or as a part of a fusion peptide or polypeptide which renders the plant resistant to the effects of DON. For example, the *Fusarium* fungi produce a broad range of plant diseases such as seedling and head blight on small grains such as wheat and rye, ear and stalk blight on corn (maize), stem rot of carnation, and seedling blight and root rot of a number of other plant species, including, beans, clover, peanuts, and tomato. Therefore, the present invention provides a method for making transgenic plants resistant to DON produced by *Fusarium* fungi. Since the peptide mimotope competes with DON for binding to the 60S ribosome but does not have DON's inhibitory effect, transgenic plants expressing the present invention are resistant to the effects of DON. Transgenic plants that express the peptide mimotope, either as an isolated peptide or as part of a fusion peptide or polypeptide, include, but are not limited to, wheat, rye, corn, carnation, beans, clover, and tomato.

Therefore, the transgenic plant of the present invention comprises a nucleic acid that encodes a peptide mimotope which has the amino acid sequence $SWGPX_1PX_2$ (SEQ ID NO:6) wherein $_1X$ and $_2X$ is each any amino acid or analog thereof, preferably wherein $X_1$ is an amino acid or analog thereof which has a side chain that is a hydrogen or alkyl, most preferably, wherein $X_1$ is L, F, or analog thereof. In particular, the amino acid sequence which is set forth in SEQ ID NO:2, SEQ ID NO:4, or SEQ ID NO:5. In a preferred embodiment, the peptide mimotope is encoded by a nucleic acid comprising the nucleotide sequence selected from the group consisting of SEQ ID NO:1 and SEQ ID NO:3. As disclosed supra., the nucleic sequence encoding the peptide mimotope can be covalently linked in frame with a sequence encoding a heterologous peptide or polypeptide.

Expression of the peptide mimotope, or peptide or polypeptide comprising the peptide mimotope, in the plant cell requires the nucleic acid encoding the mimotope be operably linked to a transcription promoter that is functional in plant cells. Examples of promoters which are useful are viral promoters such as the cauliflower mosaic virus 35S promoter, heat shock protein promoters such as the HSP70 promoter, light induced promoters such as the ST-Ls1 or the rubisco small subunit promoter, stress response promoters such as the PR promoter, the *Agrobacterium tumefaciens* nos promoter, and various organ, root, tuber, and leaf specific promoters. The DRE promoter element that is inducible under stress is an example of a plant promoter that responds to environmental conditions (Yamaguchi-Shinozaki et al., Plant Cell 6: 251-264 (1994)). The nucleic acid encoding the peptide mimotope is preferably operably linked at the 3' end to a transcription termination signal. An example of such a sequence is the transcription termination signal of the octopine synthase gene.

There are many methods known in the art for transforming a plant cell with heterologous nucleic acids. Common methods include transformation with T-DNA containing the DNA of interest and using *Agrobacterium tumefaciens* as the means for transformation or with Ti or Ri plasmids using the bacterium *A. rhizogenes* as the means for transformation. A suitable plasmid for transformations is the pART27/7 plasmid vector isolated from *Agrobacterium tumefaciens*. Other methods for transforming a plant cell include cell fusion, electroporation, biolistic or conventional injection.

*Agrobacterium* related methods require special plasmid vectors such as intermediate or binary vectors. Intermediate vectors require integration into Ti or Ri plasmids by homologous recombination into the region containing the T-DNA. The intermediate vector is transferred into the *Agrobacterium* by means of conjugation in the presence of a helper plasmid. The transformed *Agrobacterium* is then used to transform the cell. The preferred method for transforming *Agrobacterium* is using plasmids of the binary type. Binary vectors replicate both in *Escherichia coli* and *Agrobacterium*. Therefore, these vectors containing the desired DNA can be constructed using conventional molecular biology techniques and the recombinant plasmid directly transferred to *Agrobacterium*. Binary vectors usually contain a marker gene and a polylinker for inserting the desired DNA flanked by the left and right T-DNA border regions. Both the intermediate and binary vectors contain the vir region which is necessary for transfer of the T-DNA into the plant cell.

Transformation of plant cells with transformed *Agrobacterium* is by co-cultivation of the cells with the transformed *Agrobacterium* which results in transfer of the T-DNA containing the desired nucleic acid into the plant cell. Sources for plant cells are explants which can include but is not limited to sections of leaves, stems, roots, segments of petioles, flowers and flower parts, and cotyledon tissue. Whole plants are regenerated from the infected plant material or from protoplasts or suspension-cultivated cells in a suitable medium which can contain antibiotics or biocides (e.g., kanamycin, bleomycin, hygromycin, chloramphenicol) for selection of the transformed plant cells. The ability and efficiency of regenerating a transformed or transgenic plant using transformed isolated cells or explants is dependent on the species of plant and the type of transformed cell. Transformation of plants can be achieved according to the *Agrobacterium*-mediated method disclosed in U.S. Pat. No. 5,684,238 to Ausich et al and U.S. Pat. No. 5,618,988 to Hauptmann et al.

Non-*Agrobacterium* mediated transformation such as electroporation, injection, cell fusion, or particle bombardment do not require special plasmids and, therefore, can use standard plasmids such as the pUC derivatives and conventional cloning techniques. For example, to make the transgenic plants of the present invention using the Biolistic bombardment method, plant tissue is transformed using the Biolistic method described in U.S. Pat. No. 5,767,368 to Zhong et al. Further examples of the Biolistic bombardment method are disclosed U.S. Pat. No. 5,736,369 to Bowen et al.

The following examples are intended to promote a further understanding of the present invention.

EXAMPLE 1

Identification of peptide mimotopes which bind to mycotoxin DON-specific monoclonal antibody. Monoclonal antibody 6F5 (mAB 6F5) was used to select for peptides that mimic the mycotoxin from a library of filamentous phages that have random 7-mer peptides on their surfaces.

A phage-display heptapeptide library containing $2\times10^9$ independent clones that express random peptide 7-mers fused to minor coat protein g3p of filamentous coliphage M13 was purchased from New England Biolabs, Inc. Beverly, Mass. The library had sufficient complexity to contain most if not all of the $20^7=1.28\times^9 10$ possible 7-mer sequences. After amplification in *Escherichia coli* ER2537 (purchased from New England Biolabs, Inc.), the phage in the library were selected by panning elution as below.

One hundred microliters of a preparation containing mAB 6F5 (prepared as shown in Casale et al., *Op. cit.*) at 15 μg/ml in 0.01 M phosphate-buffered saline (PBS) (pH 7.4) was dispensed into each well of disposable IMMUNO-4 microtiter strips (Dynatech Laboratories, Inc., Chantilly, Va.). The antibody was dried overnight onto the wells in a forced-air oven at 40° C. Blank wells were coated with an equal concentration of mouse IgG. The wells were washed 4 times by filling each well with 300 μl PBS and aspirating the contents. Nonspecific binding was blocked by incubating 320 μl of 10% non-fat dry milk dissolved in PBS (10% milk-PBS) in each well for 1 hour at 37° C. and then washing the wells four times with PBS. For panning-elution selection, the recombinant phage display peptide library, which had been diluted with 10% milk-PBS to about $10^{10}$ PFU/ml, was added to the wells (100 μl/well) and the wells incubated at 37° C. for 1 hour. Afterwards, the wells were washed 20 times by filling each well with about 300 μl of PBS containing 0.1% Tween 20 (PBST), followed by incubation with 300 μl of PBS per well at 37° C. with shaking at 150 rpm for 1 hour. The wells were then washed 10 times with about 300 μl PBS-T per wash. To elute the bound phage, 100 μl of DON (100 μg/ml in PBS containing 1% methanol) or PBS containing 1% methanol was added to each well, and incubated at 37° C. with shaking at 150 rpm for 1 hour. The eluted phage were collected from the microtiter wells and used to infect *E. coil* ER2537 for phage titer and amplification experiments. The amplified phage, which contained about 8 ηg/ml of DON, was used for a subsequent round of panning-elution selection. After four rounds of panning-elution selection, individual plaques were picked from Luria-Bertani plates and used to infect *E. coil* ER2537 cells in phage production experiments.

Binding to mAB 6F5 was determined for each individual phage clone by ELISA. The amounts of bound phage in mAB 6F5-coated microtiter wells were determined by incubation with 100 μl of sheep anti-M13 horseradish peroxidase (HRP) conjugate, which had been diluted 1:5,000 in 10% milk-PBS, per well at 37° C. per hour, followed by incubation with 100 μl of 3,3',5,5'-tetramethylbenzidine substrate per well at 37° C. for 15 minutes. The absorbance at 450 ηm was determined after the reaction was stopped by adding 100 μl of 10% sulfuric acid per well.

After specific binding to mAB 6F5 was confirmed by ELISA, 10 ml of recombinant phage particles ($10^{11}$ PFU/ml in LB medium) from each positive phage clone was used for single-stranded DNA isolation performed with a QIAPREP Spin M13 kit (Qiagen, Inc., Chatsworth, Calif.). The single-stranded DNA was sequenced with −28 gIII and −96 gIII sequencing primers (New England Biolabs, Inc.) by using Taq cycle sequencing and dye terminator chemistry at the Michigan State University DNA Sequencing Facility.

Five phage isolates were identified to bind to mAB 6F5 by ELISA. These isolates were designated DONPEP.1, DONPEP.2, DONPEP.3, DONPEP.4, and DONPEP.12. Four of the five isolates had the same nucleotide sequence which was 5-AGTTGGGGTCCTTTTCCGTTT-3 (SEQ ID NO:1), which encodes the peptide with the amino acid sequence SWGPFPF (SEQ ID NO:2) while isolate DONPEP.12 had the nucleotide sequence 5'-TCTTGGGGTCCGCTTCCTTTT-3' (SEQ ID NO:3), which encodes the peptide with the amino acid sequence SWGPLPF (SEQ ID NO:4).

EXAMPLE 2

This example demonstrates that DON mimotope peptides actually mimicked the epitope recognized by mAB 6F5 and was not nonspecifically bound to the surface of the antibody molecule outside the antigen binding site. Competitive ELISAs were used to show that both phage isolates encoding either peptide competed with DON for the antigen binding site.

To perform a competitive direct ELISA (CD-ELISA) with the phage-displayed peptide, INMUNO-4 microtiter wells were coated with mAB 6F5 and blocked as described in Example 1. Various concentrations of DON (0 to 10,000 ng/ml in 1% methanol-PBS) were mixed with equal volumes of phage-displayed peptide (diluted 1:10 in 10% milk-PBS). The mixtures were added to mAB 6F5-coated microtiter wells (100 μl/well), and the preparations were incubated at 37° C. for 1 hour. Afterwards, the wells were washed 6 times with PBS-T (about 300 μl/well) and then amounts of bound recombinant phage were determined by incubating the preparations with 100 μl of sheep anti-M13 HRP conjugate (diluted 1:5,000 in 10% milk-PBS) per well at 37° C. for 1 hour. The amounts of bound enzyme were determined as described in Example 1. For comparison, 50 μl of DON-HRP per well was also mixed with 50 μl of DON at various concentration (0 to 10,000 ng/ml in 1% methanol-PBS) per well, and the preparations were incubated in mAB 6F5-coated microtiter wells at 37° C. for 1 hour. The amounts of bound enzyme were determined as above.

To perform a competitive indirect ELISA (CI-ELISA) with phage-displayed peptide, 100 μl of phage-displayed peptide was dispensed into each well of disposable IMMUNO-4 microtiter strips, and the peptide was dried onto the wells in a forced air oven at 40° C. overnight. The strips were washed and blocked as described for the CD-ELISA. Various concentrations of DON (0 to 10,000 ng/ml in 1% methanol-PBS), 50 μl/well, was added to the wells, and then 50 μl of anti-DON mAB 6F5 (10 μg/ml in 10% milk-PBS) was added to each well. The wells were incubated at 37° C. for 1 hour. Then the wells were washed six times with PBS-T, and the amounts of bound anti-DON mAB 6F5 were determined by incubation with goat anti-mouse IgG-HRP conjugate (diluted 1:2,000 with 10% milk-PBS) at 37° C. for 1 hour. The amounts of bound enzyme were determined as described above.

Figure 2:
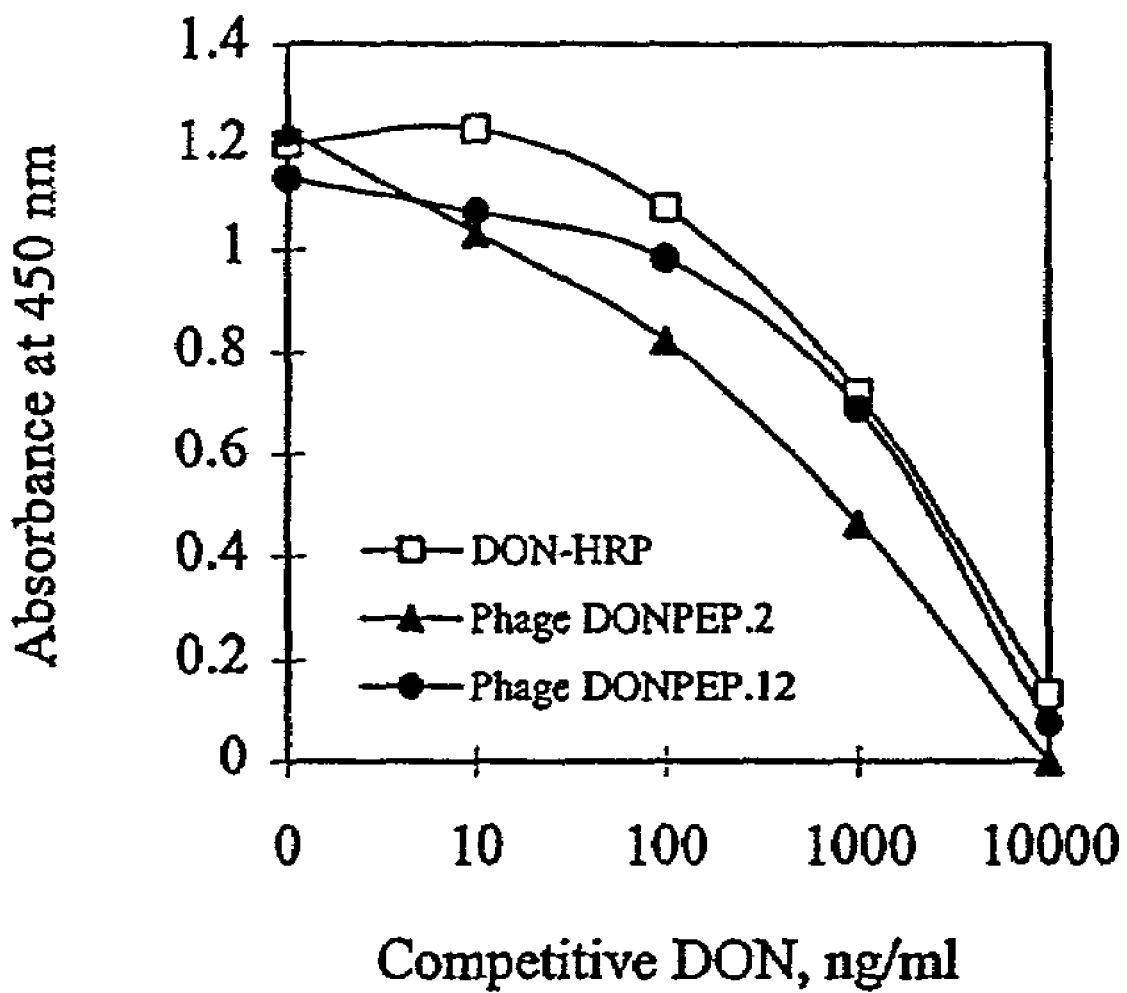
FIG. 2 shows the competition between phage-displayed peptide mimotopes and DON for binding to immobilized mAB 6F5 in a CD-ELISA. Various concentrations of free DON competed with equal volumes of phage-displayed peptides (at a constant concentration) for binding to immobilized mAB 6F5. Bound phage peptide was detected with HRP-conjugated sheep anti-M13 IgG and then measured by absorbance. DON-HRP was included as a positive control.
Figure 3A:
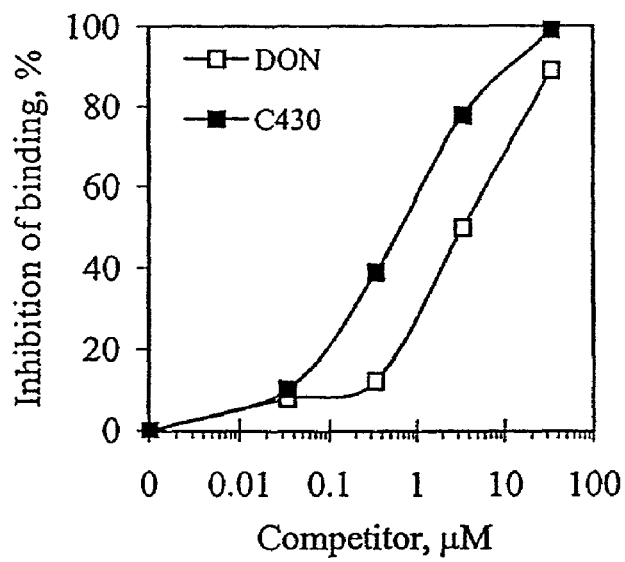
FIG. 3A shows synthetic peptide C430 and DON competing with DON-HRP for binding to immobilized mAB 6F5.
Figure 3B:
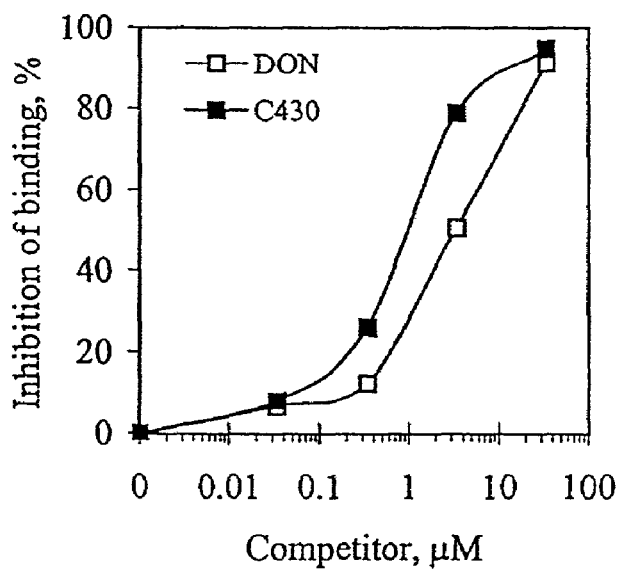
FIG. 3B shows synthetic peptide C430 and DON competing with C430-HRP for binding to immobilized mAB 6F5.
Figure 4:
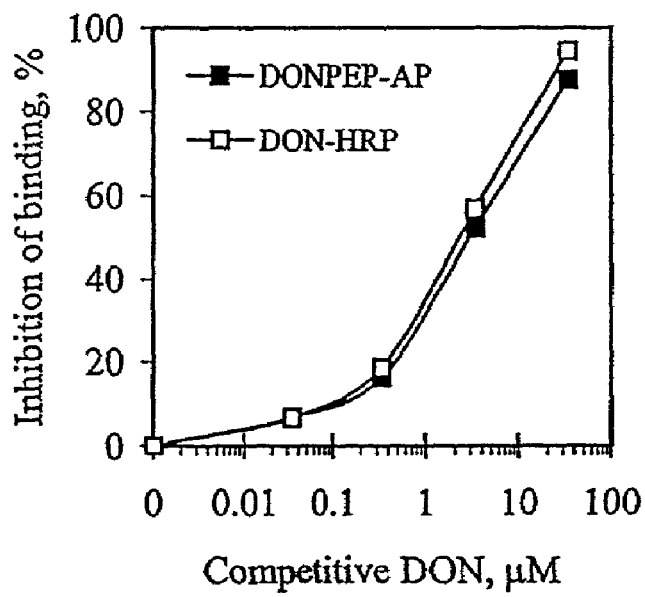
FIG. 4 shows a CD-ELISA performed with DONPEP-AP fusion protein. Binding of the DONPEP-AP fusion protein to immobilized mAB 6F5 was inhibited by free DON. Competition of free DON with DON-HRP was used as a control.

The results are shown in FIG. 2. The binding of phage clones DONPEP.2 and DONPEP.12 to immobilized mAB 6F5 was competitively inhibited by free DON. This strongly suggested that these two phage clones bind to the antigen binding site of the mAB, mimicking, in part, the structural epitope of DON.

EXAMPLE 3

This example demonstrates that a synthetic peptide, C430, which comprises the amino acid sequence SWGPFP (SEQ ID NO:2), was alone was sufficient for binding to the mAB, independent of the phage structural context.

C430, a DON peptide mimotope with a structurally flexible linker and a cysteine residue, which has the sequence $NH_2$-SWGPFPFGGGSC-COOH (SEQ ID NO:5) was synthesized via N-(9-fluorenylmethoxycarbonyl) (Fmoc) chemistry at Bio-Synthesis, Inc. of Lewisville, Tex. C430 was used at various concentrations to compete with DON-HRP for binding to mAB 6F5 in a CD-ELISA. C430 was also conjugated to HRP with a sulfo-MBS cross-linker. The procedure used for the CD-ELISA performed with the C430-HRP conjugate was the same as the procedure used for the ELISA performed with DON-HRP described above, except that C430-HRP (diluted 1:5,000 in blocking buffer) replaced the DON-HRP.

The results shown in FIG. 3A show that binding of DON-HRP to immobilized mAB 6F5 was inhibited by free C430, and the results shown in FIG. 3B show that binding of C430-HRP conjugate was inhibited by free DON. This indicates that the peptide alone was sufficient for binding to the mAB, independent of the phage structural context. When C430 was used to compete with DON-HRP or C430-HRP conjugate for binding to mAB 6F5, the 50% inhibitory concentrations were 0.64 to 0.8 μM, whereas 3.4 μM free DON was required to obtain 50% inhibition of DON-HRP or C430-HRP conjugate binding to the same mAB. This indicates that mAB 6F5 has a higher affinity for C430 than for DON. In a similar CD-ELISA, none of the individual amino acids in C430 (at concentrations up to 34 μM) significantly inhibited binding to DON-HRP. This suggests that the sequence in C430 was important for specific binding to mAB 6F5, since individual amino acids did not bind mAB 6F5 specifically (data not shown).

EXAMPLE 4

This example demonstrates that the DON mimotope peptide is structurally stable in a protein context different from the phage protein context or as a free peptide.

A 179-bp DNA fragment encoding the g3p signal peptide, DONPEP.2, and the first 17 amino acids of M13 phage g3p protein from the DONPEP.2 phage isolate was amplified by polymerase chain reaction (PCR) performed with Pfu DNA polymerase, a sense primer, 5-GCCAAGCTTAGATCTTG-GAGCCTTTTTTTTGGAG-3' (SEQ ID NO:7), and an antisense primer, 5'-CCGGTCGACCTGTATGG-GATTTTGCTAAACAACT-3'(SEQ ID NO:8). After gel purification, the amplified DNA was digested with BglII and SalT and was cloned into BamHI-SalI-digested pLIPS (Carrier et al., J. Irumunol. Methods 181: 177-186 (1995)), which generated plasmid pQY7 containing the nucleic acid sequence encoding DONPEP.2 covalently linked to the 5' end of the nucleic acid sequence encoding alkaline phosphatase. The ligated product was used to transform *E. coil* DH11S competent cells (GIBCO BRL, Gaithersburg, Md.), which generated DH11S/pQY7. DONPEP-alkaline phosphatase (AP) fusion protein was produced from DH11S/pQY7 grown in SB medium (35 g bactotrypase, 20 g bacto yeast extract, 5 g NaCl per liter) containing 100 μg/ml ampicillin and induced by 1 mM isopropyl-βD-thiogalactopyranoside (IPTG). The peripiasmic DONPEP-AP fusion protein was extracted by suspending the bacterial cells (1:5, vol:vol) in lysis buffer (50 mM Tris-HCl [pH 8.01], 20% sucrose, 10 mM EDTA, 0.1 mg/ml lysozyme, 0.5 mM phenylmethylsulfonyl fluoride). After 1 hour on ice with agitation, the preparation was centrifuged at 7,000×g for 30 minutes. The supernatant fraction was filtered through a 0.4 μm-poresize porous filter. The ability of the DONPEP-AP fusion peptide to compete with DON for binding to mAB 6F5 was determined by CD-ELISA performed as previously described. Briefly, IMMUNO-4 wells were coated with mAB 6F5 and washed as described above. Serial dilutions of DON (0 to 10,000 ηg/ml in 0.05 M Tris-buffered saline pH 7.4 (TBS) were each mixed with equal volumes of DON-PEP-AP fusion protein (periplasmic extract diluted 1:7 with 2% nonfat dry milk-TBS). The mixtures (100 μl/well) were added to the mAB 6F5 coated microtiter wells and incubated at 37° C. for 1 hour. After the wells were washed six times with 300 μl of TBS containing 0.1% Tween 20, the amounts of bound DONPEP-AP for each mixture were determined by incubation with a p-nitrophenyl phosphate substrate solution at 37° C. for 45 minutes. The absorbance at 405 run was determined.

The results, which are shown in FIG. 4, show that the DONPEP-AP fusion protein had alkaline phosphatase activity, but more importantly, the results show that its specific binding to mAB 6F5 was similar to that of DON-HRP. This indicates that the DON peptide mimotope sequence is structurally stable in a different protein structural context.

EXAMPLE 5

This example demonstrates the feasibility of using DON mimotope peptide sequence as immunochemical reagents for DON immunoassays in food and feed.

A CD-ELISA was performed as above using wheat extracts spiked with DON. As shown in FIG. 5, both the C430-HRP conjugate and DONPEP-AP fusion protein exhibited binding to immobilized mAB 6F5 in the wheat extract which was similar to the binding of DON-HRP. All three HRP conjugates produced similar linear inhibition curves at DON concentrations ranging from 0.1 to 10 μg/ml in wheat extract. However, a slightly lower level of absorbance was observed in the CD-ELISA performed with C430-HRP and DONPEP-AP in wheat extract than in PBS buffer, indicating that the wheat extract interfered with binding of the peptide mimotope to anti-DON mAB 6F5 to some extent.

EXAMPLE 6

This example was performed to determine whether the DON peptide mimotope sequence can elicit an immune response in animals similar to that of DON and, therefore, be useful as an alternative antigen for DON.

Synthetic peptide C430 was conjugated to BSA with a m-maleimidobenzoyl-N-hydroxysulfosuccinimide ester (sulfo-MBS) cross-linker. The C430-BSA conjugate, at a molar ratio of peptide C430 to the carrier protein BSA of about 29:1, was used to inject 7-week-old BALB/c female mice intraperitoneally or 6-month-old New Zealand white rabbits subcutaneously. The initial injections used for the mice contained 100 to 200 μg of C430-BSA conjugate in 200 μl of saline-Freund's complete adjuvant (1:1). These injections were followed at 3-week intervals by booster injections consisting of 100 to 200 μg of conjugate in 200 μl of saline-Freund's incomplete adjuvant (1:1). The initial inoculum used for rabbits consisted of 1 mg of the C4430-BSA conjugate in 1 ml of saline Freund's complete adjuvant (1:1) followed by booster injections at 4-week intervals consisting of 250 μg of conjugate in 1 ml of saline-Freund's incomplete adjuvant. The animals were bled 1 week after each booster injection. The antisera were screened for specific binding in phage-displayed DONPEP.2 coated wells by CI-ELISA as described above in which C430 or DON was used as the complete adjuvant.

Both the mice and rabbits produced antibody specific to the DON peptide mimotope sequence after the second injection of C430-BSA conjugate. FIG. 6 shows that after the fourth injection, the anti-serum exhibited a strong antibody response against the DON peptide mimotope sequence. A synthetic peptide C430 concentration of 0.39 μM resulted in 50% inhibition of antiserum binding to the immobilized phage-displayed peptide. However, binding of antisera to immobilized phage-displayed peptide was not inhibited by free DON in solution, indicating that the antibodies in the immunized animals were not specific for DON. Thus, the peptide mimotope sequences do not represent a true image of the DON surface structure.

EXAMPLE 7

This example was to determine whether the DON peptide mimotope sequence has any cytotoxic effect. It has been known that one of the effects of DON is to cause cytotoxicity through cell apoptosis and whether the peptide mimotope sequences were like DON and had an effect on new protein synthesis.

Comparisons of the cytotoxic effect by the peptide mimotope sequences to the effects by DON were performed on mouse bone marrow cells. Ten-week-old B6C3F1 mice were euthanized by cervical dislocation, and the femurs were removed. The bone marrow cells were flushed from the femurs by using a 1-ml syringe and a 25-gauge needle. Erythrocytes were lysed with 0.83% ammonium chloride. Cell number and viability were determined by trypan blue dye exclusion by using a hemacytometer. The cells were cultured at a concentration of $10^6$ cells/ml in 96-well flat-bottom plates in RPMI-1640 in a humidified incubator containing 5% $CO_2$. RPMI-1640 was supplemented with 100 units penicillin per ml, 100 μg of streptomycin per ml, 50 μM 2-mercaptoethanol, 1 mM sodium pyruvate, 1 mM nonessential amino acids, 2 mM glutamine, and 10% fetal bovine serum. DON and synthetic peptide C430 were separately diluted in RPMI-1640. The final concentrations of C430 were 0.34, 3.4. and 34 μM and the final concentration of DON was 3.4 μM. Controls consisted on RPMI-1640. Duplicate cultures were treated. After 18 hours of exposure to DON or C430, cell viability was determined by using an MTT [3-(4,5-dimethylthiazol-2-yl)-2,5-diphenyltetrazolium bromide] conversion assay as described by Marin et al. in Toxicology 114: 67-79 (1996).

As expected, DON at a concentration of 3.4 μM caused 40 to 60% cell death after 18 hours of incubation. In contrast, synthetic peptide C430 did not have any adverse effect on the viability of the bone marrow cells at any of the concentrations tested after 18 hours incubation. When combined with DON, C430 at any of the above test concentrations did not significantly increase or decrease the cell viability caused by DON. This indicates that there was no significant synergism or antagonism between the DON peptide mimotope and DON with respect to bone marrow cell death.

EXAMPLE 8

This example was to determine whether the DON peptide mimotope sequence were like DON and had an effect on new protein synthesis.

To determine the effects on protein synthesis, in vitro translation assays were performed using γ-globulin mRNA template. DON or synthetic peptide C430 (0 or 3.4 μM in a 50-μl (final volume) reaction mixture) was added to 30 μl of a biotin translation mixture (Boehringer Mannheim Corp., Indianapolis, Ind.) containing reticulocyte lysate, 10 pmol of biotin-lysine-$tRNA^{lys}$, 42 μM amino acids (without lysine), spermidine, energy mixture, dithiothreitol, 83 mM potassium acetate, and 83 mM magnesium acetate. The mixtures (46 μl ) were incubated on ice for 10 minutes, and then 4 μl of γ-globulin mRNA (0.5 μg/ml) was added. The final reaction mixture (50 μl) was incubated at 30° C. for 1 hour. The translated protein samples were stored at −80° C. before analysis by Western blot.

For Western blot analysis, 3 μl aliquots of protein from the in vitro translation assays were boiled for 10 minutes after mixing with sodium dodecyl sulfate (SDS)-polyacrylamide gel electrophoresis loading buffer. The samples were then loaded into the wells of a mini SDS-10% polyacrylamide gel and electrophoresed at 80 volts for 2 hours. The in vitro synthesized proteins were detected by electrotransfer to a polyvinylidene difluoride transfer membrane (DuPont NEN Research Products, Boston, Mass.) followed by incubation with strepavidin-peroxidase conjugate (Boehringer Mannheim Corp.). Bound enzyme was visualized by incubation with SUPERSIGNAL ULTRA chemiluminescent substrate (Pierce Chemical Co., Rockford, Ill.) and by exposing to Kodak XAR5 autoradiography film (Kodak Corp., Rochester, N.Y.).

As shown in FIG. 7, DON at a concentration of 3.4 μM significantly inhibited new protein synthesis whereas 3.4 μM of C430 had no such inhibitory effect. Unexpectedly, when 3.4 µM DON was mixed with an equimolar amount of C430, new protein synthesis was not inhibited. This indicates that at least in vitro, C430 has an antagonistic to the inhibitory effect of DON on protein synthesis.

EXAMPLE 9

This example provides a structural model of the DON peptide mimotope sequence and compares the structural model with the structure of DON.

To do homologous sequence searching and peptide modeling, the computer program SEQUERY (Collawn et al., EMBO J. 10: 3247-3252 (1991); Craig et al., J. Molec. Biol. 281: 183-201 (1998)) was used to search for amino acid sequences similar to the DONPEP.2 sequence SWGPFPF (SEQ ID NO:2) in a database of nonhomologous protein structures derived from the ≦25% identity set of the Protein Data Bank (PDB) Select list. SEQUERY identified all occurrences of protein sequences in the PDB that matched the tetrapeptidyl fragments of DONPEP.2. The following conserved amino acid residue substitutions were allowed during the sequence search: S for T, W for F, P for ST, and F for ST. The resulting sequence analogs consisted of tetrapeptides that matched a portion of DONPEP.2 and had known three-dimensional structures which were available in the Brookhaven PDB. The secondary structures of these sequence analogs were subsequently analyzed using the Superpositional Structural Assignment computer program (Craig et al., J. Molec. Biol. 281: 183-201 (1998)). This program superimposed the sequence analogs onto a set of regular secondary structure templates and assigned each sequence analog to the structural category, e.g., α-helix, β-strand, reverse turn, which matched most closely within a 1.0-Å main-chain root-mean-square positional deviation (RSMD); if no template matched a 1.0-Å RSMD, the structure of the sequence analog was considered irregular. The sequence analogs that were found to be irregular were analyzed visually by using molecular graphics, so that slightly irregular structures, e.g., a bent α-helical turn, could be assigned to the most appropriate structural category.

A three-dimensional structural model of DONPEP.2 was created based on the structural sequence analogs by using the molecular modeling software INSIGHT II (available from Molecular Simulations Inc., San Diego, Calif.) and a Silicon Graphics INDIGO$^2$ EXTREME computer (Mountain View, Calif.) The overlapping amino acid residues of the sequence analogs were superimposed, and a consensus structure was created, which consisted of the peptide main-chain atoms and proline side chains. Side chains for the nonproline residues were added to the model by using the rotamer library of INSIGHT II. Final side chain positions were selected based on consensus between the sequence analogs and the absence of steric overlap. Interactions within the model were then optimized by using 100 steps of backbone-restrained steepest descent energy minimization with the cff91 force filed of the Discover 3 module of INSIGHT II. The stereochemical quality of the model was validated with PROCHECK (Laskowski et al., J. Appl. Cryst. 26: 283-291 (1993)).

The structural and chemical similarities between DON and DONPEP.2 peptide model were analyzed using POWERFIT (Microsimulations Inc., Mahwah, N.J.), which tests a large number of random three-dimensional alignments of two structures by using a Monte Carlo search algorithm. The quality of the superpositions was scored by using a complementary function measuring van der Waals and electrostatic overlap between the two structures. The three-dimensional structure of nivalenol (Cambridge Structural Database (CSD) code: DUTJOR10), which was obtained from the CSD (Cambridge Crystallographic Data Centre, 12 Union Road, Cambridge, United Kingdom, CB2 1EZ), was used in place of DON for the superposition because a three-dimensional structure for DON is not available. Nivalenol binds to mAB 6F5 with slightly less affinity than DON binds to mAB 6F5. The side chain angles of the S, W, and F amino acid residues in the peptide were allowed to rotate during POWERFIT superposition, and only superpositions with the stereochemically acceptable side chain conformation were accepted. No bonds in the rigid nivalenol structure were allowed to rotate. The results of the alignment were analyzed visually with INSIGHT II.

Within the set of nonhomologous protein structures, 31 analogs of DONPEP.2 tetrapeptides were found. The sequence search was limited to four residues because close sequence matches to more than four residues are rarely found in the Brookhaven PDB. The secondary structures of these tetrapeptides, which were assigned based on close backbone superposition with ideal secondary structures (α-helices, β-strands, reverse turns), were predominantly in the β-strand configuration (Table 1).

To construct a three-dimensional structural model of SWGPFPF from tetramer analogs in Table 1, we began by superimposing the analogs for residues 1 to 4 (SWGP) were superimposed, which all formed a β-strand. The superpositions for residues 2 to 5 (WGPF) and 3 to 6 (GPFP) indicated that the central region of the peptide could for either a β-strand or a reverse turn. However, the pair of proline residues in the sequence resulted in a significant kink even in the β-strand-like analogs (all of which had a superpositional RMSD equal to or greater than 0.9 Å in the GPFP region). Similarly, in the turn-forming analogs, the two proline residues made it impossible to form an ideal reverse turn. Thus, it seems likely that the central region forms a loose, inverted U-shaped turn flanked by residues in the β-strand conformation, which is prevalent in the analogs for residues 4 to 7 (shown in Table 1).

TABLE 1

Secondary structure assignment of DONPEP.2 sequence analogs*.

| Analog | Conformation | Backbone RMSD (Å) | | PDB Code | Chain | Residue Range |
|---|---|---|---|---|---|---|
| SWGP | | | DON mimotope peptide | | | 1–4 |
| SWGS | Strand | 0.580 | Penicillin amidohydrolase | 1pnk | B | 64–67 |
| SWGT | Strand | 1.264 | Sulfhydryl proteinase | 9pap | | 176–179 |
| SWGT | Strand | 0.946 | Xylanase | 1xnb | | 84–87 |
| TWGP | Strand | 0.794 | Bluetongue virus coat protein | 1bvp | 1 | 118–121 |
| SFGT | Strand | 0.734 | Creatinase | 1chm | A | 325–328 |
| SFGT | Strand | 0.453 | Phosphotransferase | 3pmg | A | 377–380 |
| WGPF | | | DON mimotope peptide | | | 2–5 |
| FGSF | Turn | 0.897 | Fe(III) superoxide dismutase | 1isc | A | 100–103 |
| FGSY | Strand | 0.465 | Beta-lactamase | 2blt | A | 322–325 |

TABLE 1-continued Secondary structure assignment of DONPEP.2 sequence analogs*.

| Analog | Confor-mation | Backbone RMSD (Å) | | PDB Code | Chain | Residue Range |
|---|---|---|---|---|---|---|
| FGSY | Strand | 0.730 | Flavodoxin | 4fxn | | 85–88 |
| FGTY | Strand | 0.530 | Simian virus 40 coat protein | 1sva | 1 | 221–224 |
| WGTY | Turn | 0.412 | Xylanase | 1xnb | | 85–88 |
| FGPW | Strand | 0.956 | Vitelline membrane protein 1 | 1vmo | A | 126–129 |
| WGTW | Turn | 0.820 | Glycosyl transferase | 1bpl | B | 215–218 |
| WGTW | Strand | 0.660 | Vitelline membrane protein 1 | 1vmo | A | 70–73 |
| GPFP | | | DON mimotope peptide | | | 3–6 |
| GPFP | Strand | 1.080 | Adenylosuccinate synthetase | 1ade | A | 276–279 |
| GPFP | Turn | 0.821 | N-cadherin | 1nch | A | 15–18 |
| GPFP | Turn | 0.518 | Photosynthetic reaction center | 1pcr | H | 54–57 |
| GPFT | Turn | 0.966 | Aconitase | 8acn | | 324–327 |
| GPFT | Turn | 0.702 | Monellin | 1mol | A | 9–12 |
| GPYP | Strand | 0.909 | Dioxygenase | 2pcd | M | 445–448 |
| GTFP | Strand | 1.110 | Black beetle virus coat protein | 2bbv | C | 131–134 |
| GTFP | Turn | 0.732 | Glycosyl transferase | 1xyz | A | 806–809 |
| PFPF | | | DON mimotope peptide | | | 4–7 |
| PFSF | Strand | 1.119 | N-acethlneuraminate lyase | 1nal | 1 | 112–115 |
| PFSY | Turn | 0.888 | Acid phosphatase | 1kbp | A | 218–221 |
| PFTY | Strand | 1.127 | Dialkyglycine decarboxylase | 2dkb | | 170–173 |
| PYSY | Turn | 0.528 | Transthyretin | 1ttb | A | 113–116 |
| PYTF | Strand | 0.599 | Dethiobiotin synthase | 1dts | | 73–76 |
| PYTF | Strand | 0.498 | Zinc endopeptidase | 1iae | | 16–19 |
| PYTF | Strand | 0.554 | Acid phosphatase | 1kbp | A | 127–130 |
| TYPY | Turn | 0.952 | Adenylosuccinate synthetase | 1ade | A | 234–237 |
| TYPY | Strand | 1.086 | Sulfhydryl proteinase | 9pap | | 85–88 |

*Backbone superpositional RMSD values based on least squares fit of analogs of the DON mimetic peptide, SWGPFPF, onto regular secondary structure templates. Each analog is assigned the conformation of the template with which it has the lowest backbone superpositional RMSD. The analogs for SWGP start in strand conformation, then show a preference for forming a turn starting at the glycine residue. The last section of the peptide analogs favor strand conformations.

Figure 1C:
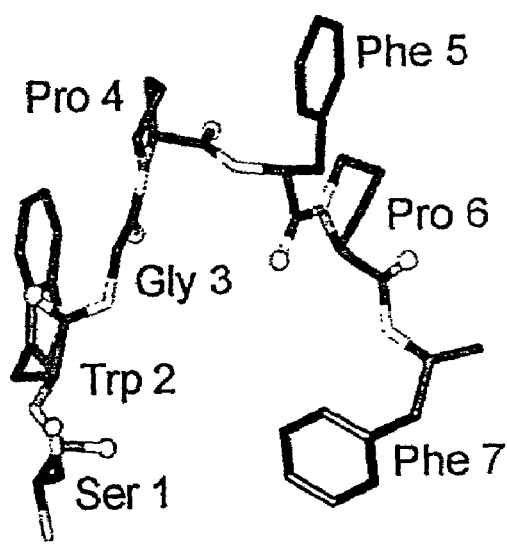
FIG. 1C shows a three-dimensional structural model of the DON peptide mimotope. The white spheres represent oxygen atoms, the white cylinders represent nitrogen atoms, and the grey cylinders represent carbon atoms.

The conformation of the turn shown in FIG. 1C is based on superposition of the turn forming analogs for residues 2 to 5.

Figure 1D:
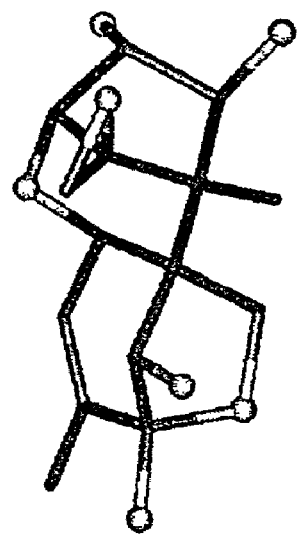
FIG. 1D shows a three-dimensional view of the crystallographic structure of nivalenol (CSD entry: DUTJOR10). The white spheres represent oxygen atoms, the white cylinders represent nitrogen atoms, and the grey cylinders represent carbon atoms.
Figure 1E:
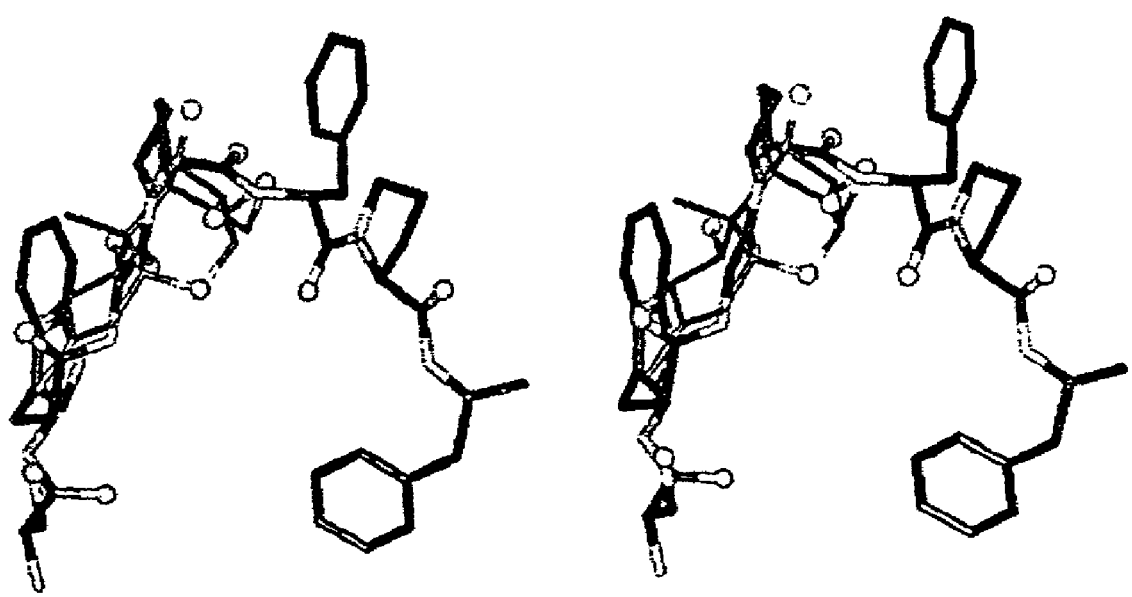
FIG. 1E shows a stereo view of the optimal PowerFit superposition of the known nivalenol structure and the DON peptide mimotope structure. Nivalenol aligns with the peptide model main-chain atoms from residues 2 to 5 of SEQ ID NO: 2 (TrpGlyProPhe or WGPF) and partially overlaps the side chains of Trp-2 and Pro-4. The white spheres represent oxygen atoms, the white cylinders represent nitrogen atoms, and the grey cylinders represent carbon atoms.

The similarity between DON and the SWGPFPF model was determined by using POWERFIT to evaluate favorable three-dimensional superposition of nivalenol (FIGS. 1B and 1D), a close analog of DON (FIG. 1A), onto the peptide model. Ten independent superpositions, beginning with random conformations, were performed by using POWERFIT. Three of the ten structures with low superpositional energies showed a preference for the DON analog to align in a specific position along the peptide backbone of the model in the region spanning from the second-residue (tryptophan) main-chain nitrogen to the fifth-residue (phenylalanine) carbonyl carbon (FIG. 1E). The remaining superpositions showed a preference for nivalenol to align along the peptide backbone as well, although it aligned with shorter sections. Also, side chain atoms of the second residue (tryptophan) in SWGPFPF overlapped with atoms of nivalenol in several of the superposition results.

EXAMPLE 10

A radio immunoassay (RIA) is performed using the C430 as follows. The RIA procedure involves incubation of monoclonal antibody mAB 6F5 simultaneously with a solution of unknown sample or known standard, and a constant amount of radioactively labled C430. After separation of the free from bound C430, the radioactivity in the respective fractions is determined. The concentration of DON in the unknown sample is determined by comparing results to a standard curve. Several known methods, including the ammonium sulfate precipitation method, double antibody technique, solid phase RIA method in which the immunoglobulin G (IgG) is conjugated to CNBr-activated SEPHAROSE gel (Pharmacia Biotech), a dextran-coated charcoal colum and albumen-coated charcoal, is used for the separation of free and bound C430 in RIA. A preferred method is an ammonium precipitation method performed according to F. Chu et al., Appl. Environ. Microbiol. 37: 104-108 (1979). In general, 50 μl of radioactive C430 (10,000 to 15,000 dpm) is incubated with 0.15 ml of anti-DON mAb solution of various dilutions in phosphate buffer (0.1 M, pH 7.2) at room temperature for 30 minutes, and then at 60° C. overnight. Separation of the bound from the free C430 is achieved by an ammonium sulfate precipitation method according to Chu et al. (ibid.). Radioactivity is determined in a liquid scintillation counter in 5 ml of AQUASOL (a product of New England Nuclear Corp., Boston, Mass.) for aqueous solutions.

EXAMPLE 11

This example provides an RIA assay for DON in a wheat sample using radioactively labeled C430. DON is extracted from the wheat sample with acetonitrile:water (84:16), defatted with hexane, and reacted with acetic anhydride in pyridine to form DON-triacetate. The reaction mixture is loaded onto a C-18 cartridge to remove excess reagents and impurities. Acetylated DON is eluted from the cartridge with 50% methanol solution, and analyzed by RIA using mAB 6F5 and radioactively labeled C430.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for making a transgenic plant cell capable of expressing a peptide mimotope of deoxynivalenol (DON) antagonistic to the inhibitory effects of DON on in vitro protein synthesis, said method comprising transforming a plant cell with a construct comprising a plant promoter operably linked to a nucleic acid that encodes the peptide mimotope SWGPFPFGGGSC as set forth in SEQ ID NO:5 as part of a fusion protein.

2. A transgenic plant cell comprising a construct comprising a plant promoter operably linked to a nucleic acid that encodes a peptide mimotope of deoxynivalenol (DON) as part of a fusion protein, wherein the peptide mimotope is SWGPFPFGGGSC as set forth in SEQ ID NO:5.

* * * * *